United States Patent
Peter et al.

(10) Patent No.: US 8,652,414 B2
(45) Date of Patent: Feb. 18, 2014

(54) DEVICE FOR STERILISING CONTAINERS

(75) Inventors: Michael Peter, Regensburg (DE);
Michael Weber, Altenthann (DE);
Sascha Hackl, Regenstauf (DE);
Thomas Morawe, Barbing (DE)

(73) Assignee: Krones AG (DE)

( * ) Notice: Subject to any disclaimer, the term of this patent is extended or adjusted under 35 U.S.C. 154(b) by 0 days.

(21) Appl. No.: 13/327,168

(22) Filed: Dec. 15, 2011

(65) Prior Publication Data
US 2012/0156110 A1 Jun. 21, 2012

(30) Foreign Application Priority Data

Dec. 16, 2010 (DE) .................. 10 2010 054 788

(51) Int. Cl.
*A61L 2/00* (2006.01)
(52) U.S. Cl.
USPC ........................................ 422/302
(58) Field of Classification Search
USPC ........................................ 422/302
See application file for complete search history.

(56) References Cited

U.S. PATENT DOCUMENTS

| 4,152,464 A | 5/1979 | Brody et al. ............... 426/413 |
| 5,879,648 A | 3/1999 | Hada et al. ............... 422/304 |
| 6,209,591 B1* | 4/2001 | Taggart ...................... 141/89 |
| 6,341,472 B1 | 1/2002 | Schroeder ................. 53/426 |
| 7,900,422 B2 | 3/2011 | Fischer ..................... 53/426 |
| 2002/0134051 A1 | 9/2002 | Kurth ........................ 53/425 |
| 2004/0089369 A1 | 5/2004 | Armbruster et al. ....... 141/82 |
| 2007/0253863 A1 | 11/2007 | Iwashita et al. ............ 422/28 |
| 2009/0110613 A1 | 4/2009 | Naka et al. ............... 422/186 |
| 2011/0094616 A1 | 4/2011 | Hayakawa et al. .......... 141/1 |
| 2011/0272861 A1 | 11/2011 | Humele ................... 264/457 |

FOREIGN PATENT DOCUMENTS

| DE | 60202995 | 7/2005 | ............. B67C 7/00 |
| DE | 102006053193 | 5/2008 | ............. B67C 7/00 |
| EP | 2 052 744 | 10/2008 | ............. A61L 2/08 |
| EP | 2 279 952 | 5/2009 | ............ B65B 55/10 |
| GB | 2/271 347 | 9/1992 | ............. B67C 7/00 |
| WO | WO 99/01374 | 1/1999 | ............. B67C 7/00 |
| WO | WO 01/44053 | 6/2001 | ............ B65B 55/02 |
| WO | WO 02/15946 | 2/2002 | ............. A61L 2/20 |
| WO | WO 2010/052068 | 5/2010 | ............. A61L 2/12 |
| WO | WO 2011/111513 | 9/2011 | ............ B65B 55/04 |

OTHER PUBLICATIONS

The Free Dictionary.com, "Dome", http://www.thefreedictionary.com/dome, retrieved Mar. 22, 2013.*
European Search Report Apr. 2, 2012 (9 pages).
German Search Report, dated Oct. 5, 2011 (6 pgs).

\* cited by examiner

*Primary Examiner* — Kevin Joyner
(74) *Attorney, Agent, or Firm* — Hayes Soloway P.C.

(57) ABSTRACT

A device for treating containers, with a housing, a sterilization chamber formed within the housing to sterilize the containers, with a transport device which transports the containers along a pre-specified transport path (P) through the sterilization chamber, and with at least one application device which applies a liquid sterilization medium to the containers during their transport through the sterilization chamber. The application device is integrated at least partly in a wall of the sterilization chamber.

15 Claims, 4 Drawing Sheets

DEVICE FOR STERILISING CONTAINERS

BACKGROUND OF THE INVENTION

The present invention relates to a device for sterilising containers. The prior art discloses plants for filling containers, for example plastic containers, with drinks. It is also known that such filling devices can be connected with sterilisation devices which sterilise the containers to be filled and in particular undertake an external disinfection of these drinks containers. The containers here are guided through a treatment chamber by carrier systems formed according to the bottle shape.

Normally such sterilisation units have comparatively large sterilisation chambers through which the containers are passed. Because of the large volumes existing within these treatment chambers or isolator chambers, it is often very difficult to achieve an atmosphere enriched with vapours. At present the containers are sprayed in a targeted manner by individually arranged nozzles, wherein these nozzles are mounted in tubes laid on the isolating chamber. In this arrangement permanent wetting of the containers is not possible. In addition adjustment of the nozzles is very time-intensive and as a result incorrect positioning can occur.

Consequently the present invention is based on the object of creating a device for sterilising containers which facilitates the generation of an atmosphere enriched with vapours. In addition the present invention is based on the object of structuring container sterilisation more efficiently.

SUMMARY OF THE INVENTION

A device according to the invention for treating containers has a housing and a sterilisation chamber formed inside the housing and preferably also by walls in the housing for sterilising the containers. Furthermore the device has a transport device which transports the containers along a specified transport path through the sterilisation chamber. In addition at least one application device is present which applies a liquid sterilisation medium to the containers during their transport through the sterilisation chamber.

According to the invention the application device is integrated at least partly in a wall of the sterilisation chamber. The liquid sterilisation medium is in particular a sterilisation fluid and particularly preferably a sterilisation fluid which contains for example peracetic acid or hydrogen peroxide.

Preferably the application device comprises one or more nozzles which apply the sterilisation medium to the containers. The nozzles are integrated directly in a wall or housing of the sterilisation chamber. In this way no unnecessary lines need be laid within the sterilisation chamber to transport the sterilisation medium to the application devices. Preferably several application devices or nozzles are provided and these are arranged particularly preferably such that they apply the sterilisation medium to the containers from below and from the side. Thus the device serves in particular for external disinfection of the containers.

Advantageously the sterilisation chamber at least in sections is formed channel-like about the transport path. Whereas in the prior art the containers are usually transported through a treatment chamber with a very large volume, here it is proposed that the sterilisation chamber is produced with comparatively small volume so that an efficient distribution of the sterilisation medium within the sterilisation chamber is possible.

Advantageously the device has a discharge device for discharging a gaseous medium from the sterilisation chamber. It is for example possible here that, for example for installation and cleaning purposes, sterilisation medium together with a carrier medium such as for example sterile air can be discharged from the chamber via said discharge device in a very short time. Preferably targeted extraction is possible of the gaseous medium present in the chamber which for example can be mixed with sterilisation medium.

A corresponding atmosphere in the sterilisation chamber can be brought into normal state in a targeted manner by a systematically arranged extraction order thus to allow faster machine access. The air flow in this case is partly or if possibly fully guided through the sterilisation chamber and extracted. During a work operation or production, the extraction is switched off or the extraction device closed. Advantageously here also the nozzle system or application devices are supplied with chemical-free water in order thus to bind or precipitate the chemical vapours and rinse the surfaces wetted with the disinfectant medium. It would however also be possible to provide a succession of several of the sterilisation chambers described here through which the containers pass successively.

In a further advantageous embodiment the device also has a supply device for the gaseous medium and this supply device is preferably spaced from the extraction device. Thus by a targeted supply of a gaseous medium, a directed flow can be achieved within the sterilisation chamber if extraction of the sterilisation medium is desired. Preferably in the housing at least one closable mounting opening is arranged. In other words the sterilisation chamber advantageously has overhaul windows to allow access to the machine.

In a further advantageous embodiment the transport device has a rotatable carrier. Here is it possible for a star column to be provided on which the carrier system is mounted and about which the carrier system rotates. The support of said star column can be designed such that the bottle can rotate past a wall or side. In this way the chamber volume not required is limited as far as possible. The star column can at the same time be a holder for the carrier system and a wall or housing of the chamber. In this embodiment the sterilisation chamber is accommodated in a housing which is stationary in relation to the carrier system.

Advantageously a number of arms is arranged on the carrier on which containers can be carried. Thus for example at the end of these arms, gripper elements or clamps can be arranged which hold the containers during transport. Therefore in this embodiment the containers are transported along a circuit through a sterilisation chamber. Advantageously a segment of the transport device comprises a wall closing the sterilisation chamber. This for example can be part of the said star column. Also in this manner it is possible to keep the sterilisation chamber or room small.

Advantageously the sterilisation chamber has a collecting chamber formed below the transport path to collect the fluid medium. Thus for example, by designing the sterilisation chamber accordingly, its base can be used as a collection chamber. The sterilisation medium or fluid can be captured and preferably returned to the treatment circuit. Due to the small treatment chamber, the air contains concentrated vapours of the treatment fluid, further intensifying the treatment and disinfection of the containers. Advantageously the application devices or treatment nozzles are arranged such that the container or containers are permanently exposed to the disinfectant medium at the side in order to make treatment as sustained as possible. It would also be possible to provide more nozzles in certain regions of the plant than in other regions.

Advantageously the nozzles for applying the disinfectant are designed such that the droplets are sufficiently large to achieve a certain mechanical effect and at the same time also generate a mist which enriches the atmosphere with vapours. This mist can settle onto the containers and also has a sterilising effect. For critical areas of the containers additional application devices or nozzles can be provided in order to spray these in a targeted manner.

In a further advantageous embodiment the housing is designed as a dome. In other words the sterilisation chamber can have a dome or cover in rounded design. These curved sides allow the spatial volume in the treatment chamber to be kept as small as possible. Furthermore the dome-like design can prevent the treatment fluid from penetrating the containers as the sprayed droplets run directly down on the curved wall and are thus prevented from dripping directly into the containers.

As stated above, the device advantageously has pipelines which supply the application devices with liquid medium and these pipelines are arranged substantially outside the sterilisation chamber. The size of the sterilisation chamber can thus be reduced further. In a further advantageous embodiment the device has a supply opening to supply the containers and a discharge opening for discharging the containers.

Here these supply and discharge openings are made as small as possible and as large as necessary in order firstly to guarantee the input and output of containers into and from the sterilisation chamber, and secondly to prevent as far as possible the entry and discharge of gas into and from the sterilisation chamber. In this way the sterilisation chamber is designed such that the treatment system is isolated from the remainder of the plant.

BRIEF DESCRIPTION OF THE DRAWINGS

Further advantageous embodiments arise from the enclosed drawings.

These show.

DETAILED DESCRIPTION OF THE DRAWINGS

Figure 1:
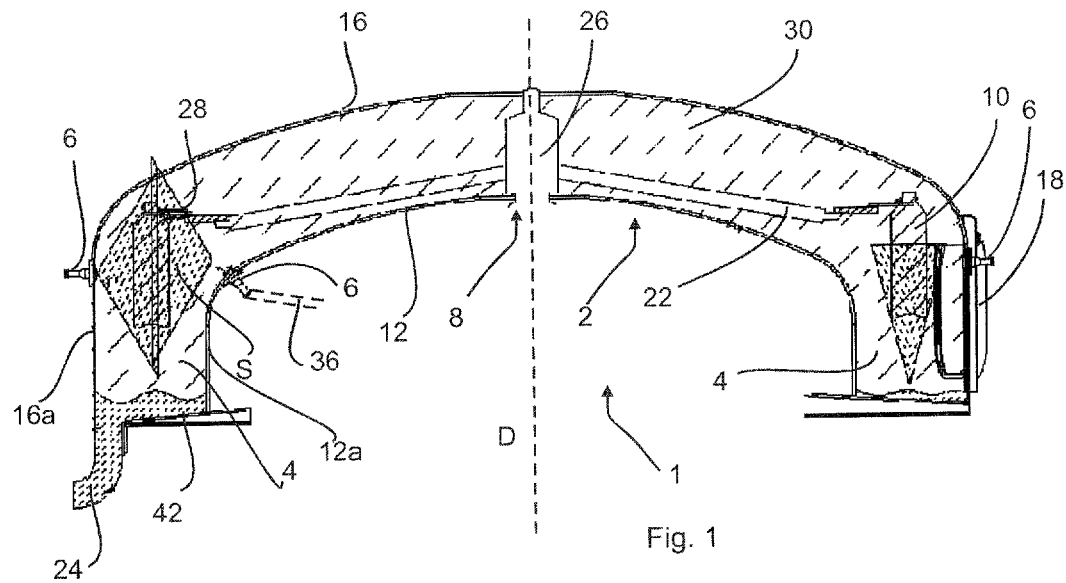
FIG. 1 a diagrammatic cross section view of a device according to the invention for sterilising containers, FIG. 2 a top view of a device according to the invention, FIG. 3 a further top view of a device according to the invention, FIG. 4 a view similar to that shown in FIG. 3, FIG. 5 a view of the interior of the device 1, FIG. 6 a further view of the interior of the device 1, FIG. 7 a further detailed view of the device shown in FIG. 6, and FIG. 8 a further depiction of the plant according to the invention.

FIG. 1 shows a diagrammatic cross section view of a device 1 according to the invention. This device 1 has a carrier 26 rotatable about a rotation axis D, on which is arranged a multiplicity of arms 22, where gripper elements 28 for holding containers 10 are in turn arranged on these arms 22. These gripper elements grip the containers 10 below the mouth. The transport device marked as a whole as 8 is used to transport the containers 10 along a circular track about rotation axis D.

Reference numeral 2 refers as a whole to a housing within which is formed a substantially closed sterilisation chamber 4 for sterilising containers.

The housing is formed by a curved base part 12 and an also curved cover part 16. These curvatures achieve that sterilisation agent deposited on the surface cannot drip down and hence where applicable into the containers, but runs out on the side, i.e. towards the outside. Below the containers the sterilisation fluid can be captured and discharged via a discharge line 24. Correspondingly the housing has a sloping floor 42 which here expels the fluid radially outwards.

In the embodiment shown the entire housing is arranged standing. It would however also be conceivable for the base part 12 to rotate with the carrier. In this case advantageously between the standing cover part 16 and the rotating base part 12 seal devices would be provided, such as water locks known from the prior art. In this case the application devices 6 which are arranged in the wall 12a of the base part 12 would also move with the containers 10. To this end it would also be conceivable to provide rotation devices which rotate the containers about their longitudinal axis during transport in order thus to achieve application to the entire peripheral wall of the containers 10. The cover part 16 here forms a side wall 16a in which are arranged several of the application devices 6. The base part 12 also forms a wall 12a in which is arranged a multiplicity of application devices 6.

Reference numeral 6 as stated refers to the application devices which apply the sterilisation fluid to the containers 10 moving inside the housing. These application devices 6 can for example be formed as spray heads or similar which apply the disinfectant or sterilisation medium to the containers over a broad surface, as indicated by reference numeral S. The lower housing part or the star column 12 here at the same time forms a limit of the sterilisation chamber 4. Within this relatively small sterilisation chamber, an atmosphere 30 of sterilisation gas can form which sterilises the containers particularly efficiently. The individual application devices 6 can be oriented onto the containers in different ways so that different regions of the containers are sterilised in succession. It would also be possible to provide application devices 6 in the floor 42.

Reference numeral 36 designates roughly diagrammatically a supply line arranged outside the housing which supplies the liquid medium to the application device 6. Here it would be possible for a central line to be provided which divides into a multiplicity of the supply lines shown in order to supply a multiplicity of application devices 6. The application devices here extend through the walls 12a, 16a, i.e. are arranged partly outside the housing and partly inside the housing 2. This achieves that the application devices take up only relatively little space inside the housing and thus the sterilisation chamber can be designed relatively small. Preferably the application devices 6 are adjustable in relation to the chamber so that the alignment of the spray cone S of the individual application devices can be modified. Preferably therefore a multiplicity of application devices 6 is provided and a transport path for the containers runs partly between these application devices 6. Preferably some application devices are arranged radially inside the transport path of the containers 10 and some application devices radially outside this transport path.

Figure 2:
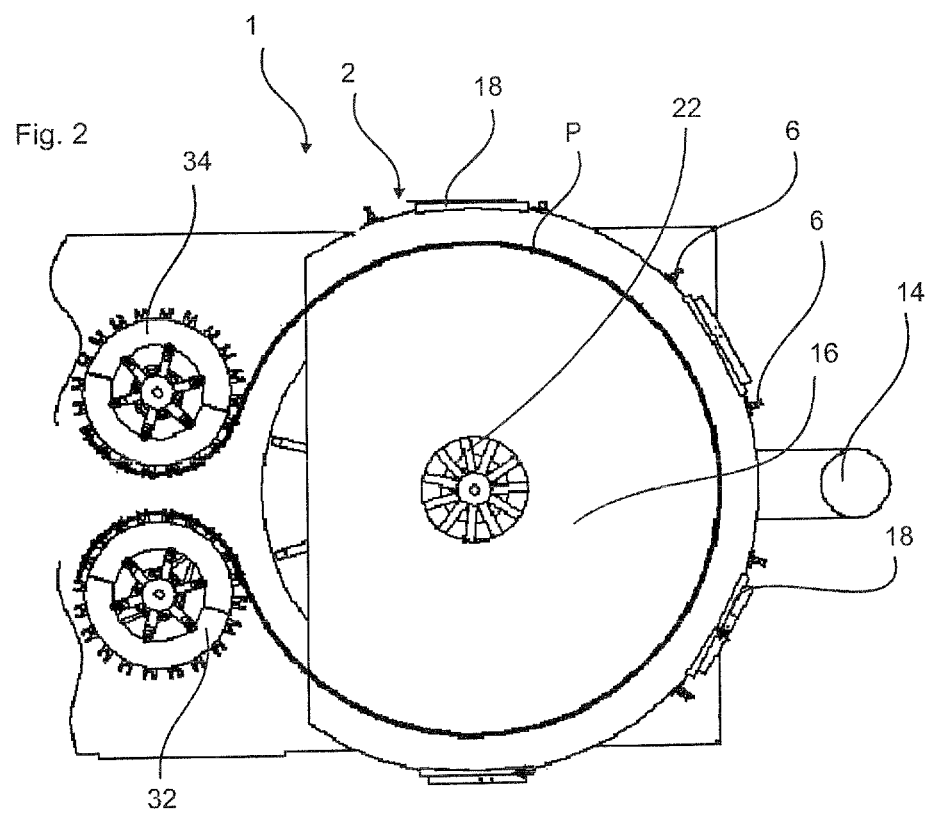

FIG. 2 shows a diagrammatic depiction of the device shown in FIG. 1. Here we can see a supply wheel 32 which supplies the containers to the sterilisation device 1 and a discharge wheel 34 which discharges the sterilised containers again. Reference numeral P designates here the circular transport path along which the containers 10 are transported. The supply wheel 32 and discharge wheel 34 are arranged such that the supply and discharge of the containers 10 lie relatively close to each other so that only a comparatively small opening need be provided in the housing 2. Through this opening furthermore sterile air can be supplied to the housing, also for example for maintenance purposes, so that on the other side gas loaded with the sterilisation medium can quickly be extracted from the plant via a discharge opening 14. Reference numeral 18 relates to openings which can be opened for example for maintenance purposes so that the user can access the machine.

The device furthermore has a reservoir for the sterilisation medium which is connected with supply lines (not shown) with the individual application devices 6.

Figure 3:
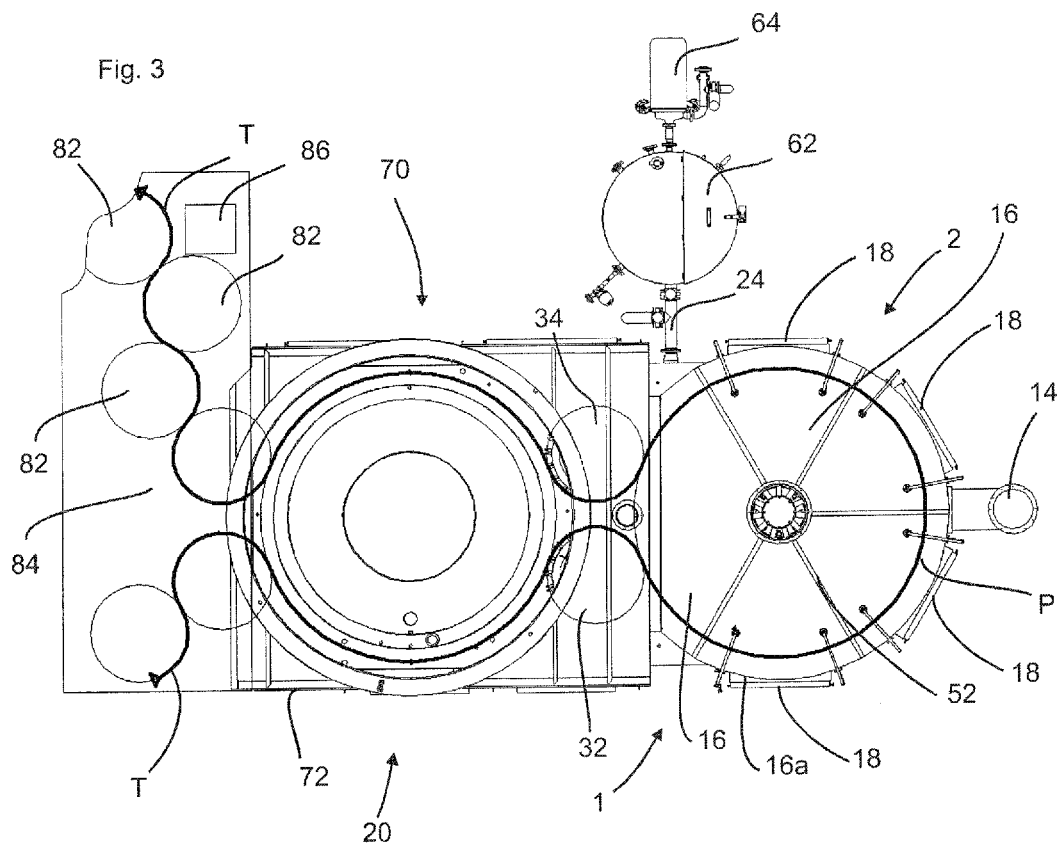

FIG. 3 shows a further top view of a device 1 according to the invention. In particular the environment of the device 1 is shown. Reference numeral T relates to the entire transport path along which the containers are transported by the plant designated 20 as a whole. The transport path P is part of this complete transport path T. At the discharge line 24 is attached a buffer container 62 and a pump 64 to extract the sterilisation medium from the device 1. Reference numeral 52 designates reinforcements which strengthen the cover part 16 of the device 1.

Reference numeral 70 as a whole designates the sterilisation device for internal sterilisation of containers. Here it would be possible for a sterilisation medium to be applied to the containers, but other methods of sterilisation are possible for example via electromagnetic irradiation or electron beam. Reference numeral 72 designates a wall of the sterilisation device 70. Reference numeral 82 relates to star wheels which discharge the containers from the plant and reference numeral 84 to a pre-machine table. Reference numeral 86 designates a filter ventilator unit which for example can be arranged on an isolator roof in the manner of a supply air system.

Figure 4:
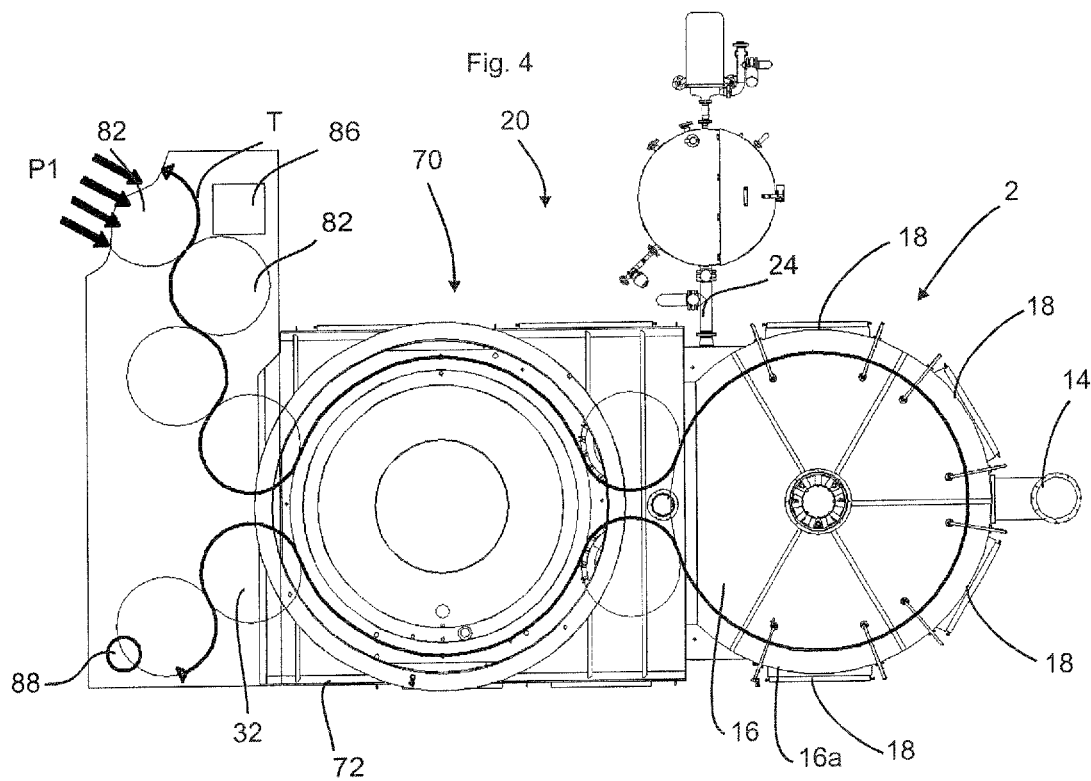

FIG. 4 shows a view similar to that in FIG. 3 wherein here however also the air flow is introduced into the entire plant 20 along arrow P1. The container transport path T opens into the plant to the machines arranged downstream such as for example a rinser, filler, closer or labelling machine. During production said air flow is then extracted at the point designated 88 at the bottom left in the figure or via extraction connector 88. This means that during production, the air flow passes through the inlet and outlet region of the container steriliser 70 and thus past the device 1 and hence does not run through the machine. If operator access is required, the inlet connector 88 is completely or partly closed. Via regulated valves in the ventilation system (not shown in detail) and an opening in inlet connector 14, the air flow is now guided through the container interior steriliser 70 and the treatment chamber of the device 1.

Figure 5:
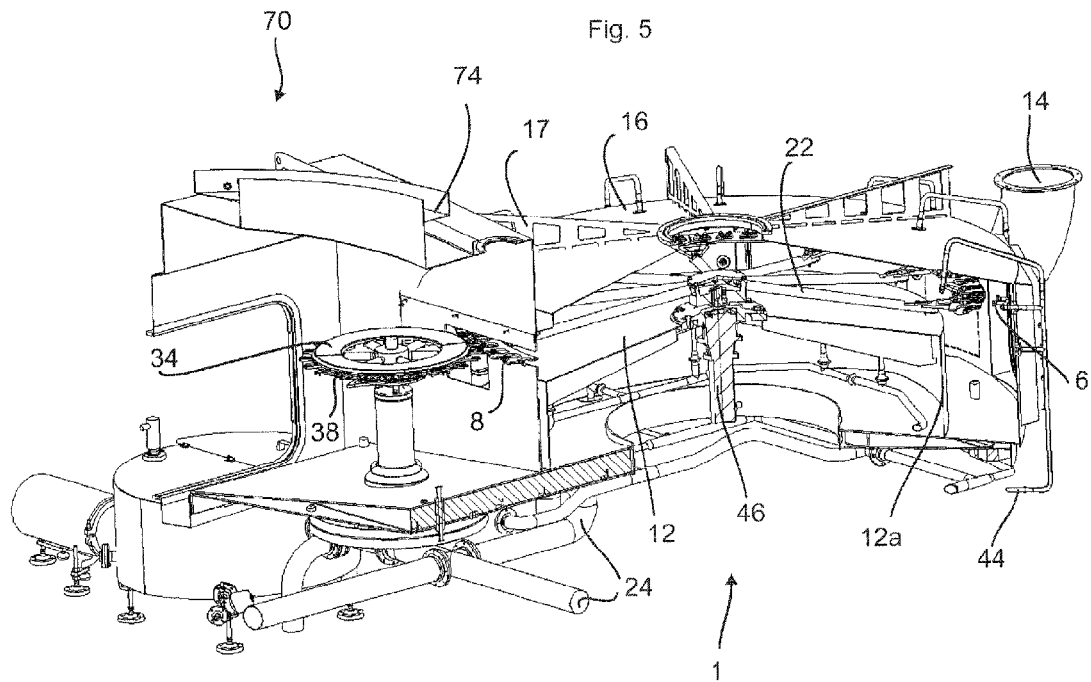

FIG. 5 shows a view of the interior of the device 1 in a further embodiment. Here again can be seen the individual arms 22 and the base part 12 of the device 1. Reference numeral 44 relates to tubing to introduce the sterilisation agent. The cover part 16 is reinforced with external reinforcement 17. Reference numeral 46 designates a drive device which serves to transport the containers through the device 1. The drive device is preferably designed as a direct drive but can however alternatively also be formed as any other (electric) motor drive. Reference numeral 24 again designates the discharge line for discharging the liquid sterilisation medium. It is evident that the device comprises a multiplicity of gripper elements 28 which serve to the hold the containers. Also at the discharge wheel 34 are corresponding gripper elements such as gripper clamps 38 which take the containers from the device 1. Reference numeral 74 designates a ring channel which for example can be part of a ring channel seal or so-called water lock to seal the interior steriliser 70.

Figure 6:
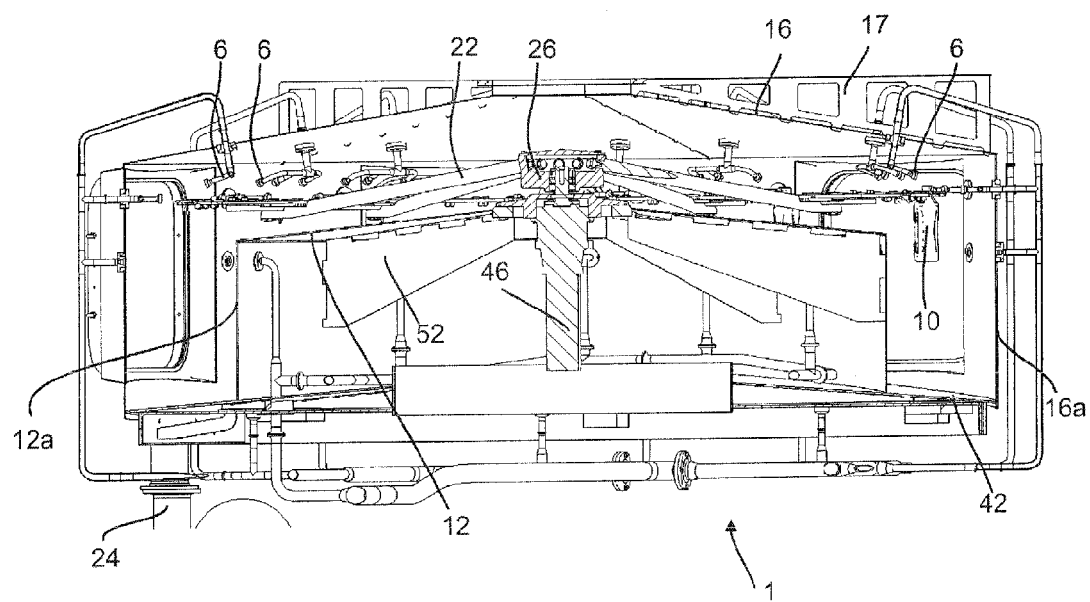

FIG. 6 shows a further view of the interior of the device 1. Here again can be seen the individual reinforcements 52. Also evident here is the sloping floor 42, over which the sterilisation medium can drain away. Also the oblique position of the cover 16 is evident.

Figure 7:
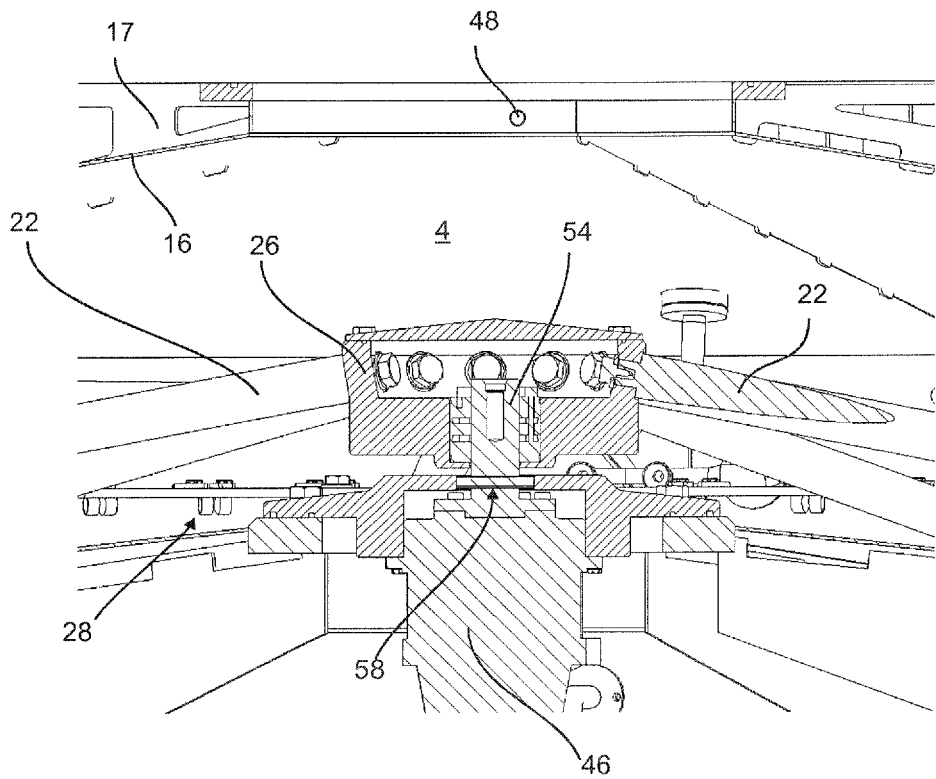

FIG. 7 shows a further detailed view of the device shown in FIG. 6. Reference numeral 54 refers to the hub of the drive device 46. Reference numeral 58 designates a ring seal. Reference numeral 28 in the picture designates a gripper element. Access to the plant is possible via a mounting opening 48.

Figure 8:
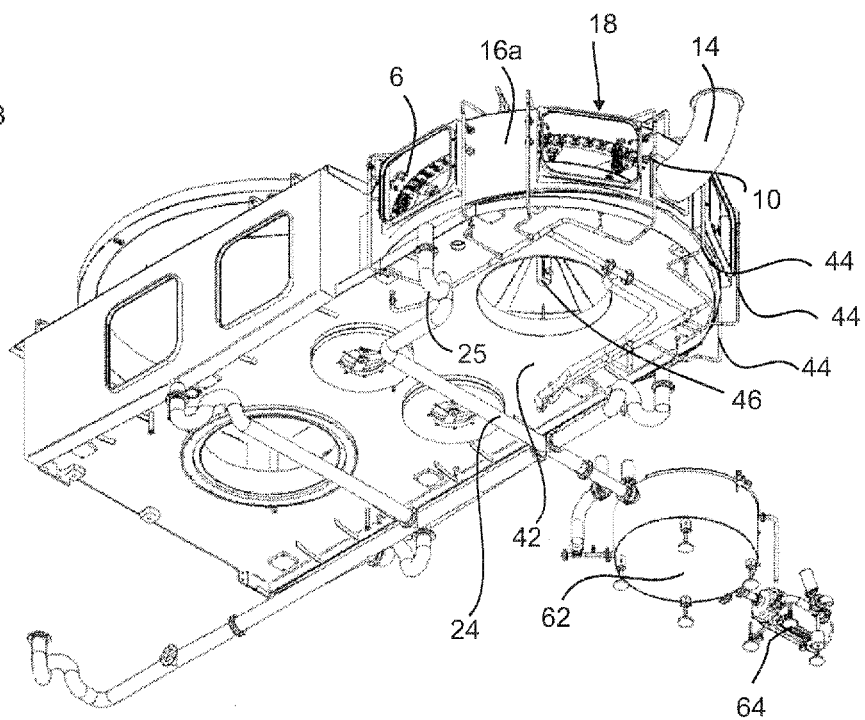

FIG. 8 shows a further depiction of the plant according to the invention. Here again can be seen the tubing shown also in FIG. 6 and the drive or shaft 46. It is evident that the shaft is arranged outside the sterilisation chamber 4. Furthermore here again the discharge lines 24 can be seen which also have a siphon 25.

The applicant reserves the right to claim all features disclosed in the application documents as essential to the invention where novel individually or in combination in relation to the prior art.

LIST OF REFERENCE NUMERALS

1 Device
2 Housing
4 Sterilisation chamber
6 Application device
10 Containers
12 Base part, star column
12a Wall
14 Discharge device, inlet connector
16 Cover part
16a Wall
17 Reinforcements
18 Opening
20 Plant, assembly
22 Arm
24 Discharge line
25 Siphon
26 Rotatable carrier
28 Gripper element
30 Atmosphere
32 Supply wheel
34 Discharge wheel
36 Supply line
38 Gripper clamp
48 Mounting opening
42 Base
44 Tubing
46 Drive device, shaft
52 Reinforcements
58 Ring seal
62 Buffer container
64 Pump
70 Sterilisation device, interior steriliser
72 Wall
74 Ring channel
82 Star wheels
84 Pre-machine table
86 Filter ventilator unit
88 Extraction connector
D Rotation axis
S Spray area
T Entire transport path, container transport path
P Transport path
P1 Arrows

The invention claimed is:

1. A device for treating containers, said device having a housing, a sterilisation chamber formed within the housing for sterilizing the containers, a transport device having a rotatable carrier for rotating the containers about their longitudinal axis during transport along a pre-specified transport path (P) through the sterilisation chamber, and at least one application device for applying a liquid sterilisation medium to the containers during their transport through the sterilisation chamber, wherein the application device is integrated at least partly in a wall of the sterilisation chamber, wherein the application device comprises one or more nozzles and wherein the nozzles are integrated directly in a wall or housing of the sterilisation chamber, extending through the wall or housing, and arranged partly outside and partly inside the wall or housing.

2. The device according to claim 1, wherein the sterilisation chamber is formed in sections about the transport path (P).

3. The device according to claim 2, wherein the discharge device is arranged such that during extraction a targeted flow of the gaseous medium through the sterilisation chamber is achieved.

4. The device according to claim 2, further including a discharge device for discharging a gaseous medium from the sterilisation chamber.

5. The device according to claim 4, further comprising a supply device for the gaseous medium, wherein the supply device is spaced from the extraction device.

6. The device according to claim 1, wherein at least one closable mounting opening is arranged in the housing.

7. The device according to claim 1, wherein a multiplicity of arms are arranged on the carrier on which the containers can be carried.

8. The device according to claim 1, wherein a segment of the transport device comprises a wall closing the sterilisation chamber.

9. The device according to claim 1, wherein the sterilisation chamber comprises a collecting chamber formed below the transport path (P) for collecting the liquid medium.

10. The device according to claim 1, wherein the housing is formed as a dome.

11. The device according to claim 1, wherein supply lines for supplying liquid medium to the application devices and are arranged outside the sterilisation chamber.

12. The device according to claim 1, wherein the device includes an opening for supply of the containers and an opening for discharge of the containers.

13. The device according to claim 1, wherein two or more application devices are provided arranged to apply the sterilisation medium to the containers from below and from a side.

14. The device according to claim 1, wherein spray from the nozzles is adjustable.

15. The device according to claim 1, wherein the application device/-s is/are adjustable in alignment relative to the chamber.

* * * * *

UNITED STATES PATENT AND TRADEMARK OFFICE
CERTIFICATE OF CORRECTION

PATENT NO. : 8,652,414 B2  
APPLICATION NO. : 13/327168  
DATED : February 18, 2014  
INVENTOR(S) : Peter et al.

Page 1 of 1

It is certified that error appears in the above-identified patent and that said Letters Patent is hereby corrected as shown below:

In the Claims

Claim 4, Col. 7, line 21, "according to claim 2" should be --according to claim 1--.

Signed and Sealed this  
Fifth Day of August, 2014

Michelle K. Lee  
*Deputy Director of the United States Patent and Trademark Office*